US00PP08699P

United States Patent [19]

de Jong

[11] Patent Number: Plant 8,699

[45] Date of Patent: Apr. 19, 1994

[54] ASTROEMERIA PLANT NAMED CAPRI

[75] Inventor: Cornelis-T.-J. de Jong, Roelofarendsveen, Netherlands

[73] Assignee: Agroplant-Select B.V., De Kwakel, Netherlands

[21] Appl. No.: 36,656

[22] Filed: Mar. 24, 1993

[51] Int. Cl.[5] ..... A01H 5/00

[52] U.S. Cl. ..... Plt./87.1

[58] Field of Search ..... Plt. 87.1

[56] References Cited

U.S. PATENT DOCUMENTS

PP. 5207 3/1984 Van Andel ..... Plt. 87.1

*Primary Examiner*—James R. Feyrer

[57] ABSTRACT

A new and distinct cultivar of Alstroemeria named Sancerre, characterized by its attractive predominantly purplish-pink flowers with outer petals having green tips and substantially purplish-pink color and neither spots nor stripes; the top inner petals are purplish-pink at the base and apex and have a broad creamy-yellow band centrally; patterns of numerous purple elongated, conspicuous spots or stripes, on the top two inner petals; and, with the bottom inner petal being purplish-pink and having fewer purple stripes as compared to the top inner petal pair.

1 Drawing Sheet

BACKGROUND OF THE INVENTION

The present invention comprises a new and distinct cultivar of Alstroemeria plant referred to by the cultivar name Sancerre. Sancerre was originated from a hybridization program in Roelofarendsveen, The Netherlands in 1985. The female parent was a cultivar named Jubilee. The male parent was proprietary hybrid number 38 which was developed and is maintained by me for sole use in planned breeding programs. Sancerre was discovered and selected as one flowering plant within the progeny of the stated parentage by me on Jul. 21, 1985 in a controlled environment in Roelofarendsveen, The Netherlands. The first asexual reproduction of Sancerre was accomplished when vegetative cuttings were taken from initial selection on Nov. 6, 1985 in a controlled environment in Roelofarendsveen in The Netherlands. Horticultural examination of selected units initiated in November 1985 has demonstrated that the combination of characteristics as herein disclosed for Sancerre are firmly fixed and retained through generations of asexual reproduction. The following observations, measurements and comparisons describe plants grown in Roelofarendsveen, The Netherlands under greenhouse conditions which approximate those generally used in commercial practice. The following traits have been repeatedly observed and are determined to be basic characteristics of Sancerre, which in combination distinguish this Alstroemeria from its parents and all other varieties of which I am aware:

1. The outer petals are heavily lobed, have finely dentate margins and have an attractive, predominantly purplish-pink color which is suffused with a slight red blush tone just below the green tips and is discernably lighter near the attachment points of these petals.
2. The inner petals are characterized by a dramatic combination of colors and pattern of stripes. The two top inner petals have a predominantly creamy white ground color in the form of a broad band, occupying the central two thirds of each of these petals, which gradually blends into purplish-pink at both the apex and basal portions of each of these petals. These two top inner petals also have numerous distinctly conspicuous elongated spots or short stripes of deep purple in a uniform pattern with stripes increasing in length and width from the attachment point to the apex of each of these petals. The lower, inner petal is substantially purplish-pink and has fewer stripes of deep purple; the central portion of this petal has lighter, washed shades of purple pink.
3. The contrasting white to creamy-yellow coloration of the wide band with dark distinct spotting of the two top inner petals, and the gradual shading of the band to the purplish-pink color that the extremes of these petals, give striking and attractive distinction to this variety which has not been seen in previous plants of this market class.

BRIEF DESCRIPTION OF THE FIGURE OF THE DRAWING

The accompanying photographic drawing of a close-up of the flower in bloom and buds shows typical inflorescence and foliage characteristics of Sancerre nearly as true as possible with illustrations of this type. In the following description, color references are made to The Royal Horticultural Society Color Chart (RHS). The color values were determined in the afternoon in May 1988 at Roelofarendsveen, The Netherlands.

BOTANICAL DESCRIPTION OF THE PLANT

Botanical: Alstroemeria cv Sancerre.
Commercial: Alstroemeria.

PLANT

A. General appearance:

*Form.*—Typical of genus, of less than average height for the market class; upright stems, continuously spreading by rhizomes, bush forming.

*Height.*—Measured from the surface of the soil to the highest flowers; Summer: about 100–120 cm Winter: about 140 cm (If grown as a bedding plant outside, the plant will have an average height of about 30–50 cm).

*Growth.*—Upright bush forming, spreading by rhizomes, vigor is average.

*Quality.*—Strong and thick stalks.

Use of this plant is for cut flower production.

B. Foliage:

*Stems.*—Mature: about 40–50 per plant, per year.

*Number of leaves.*—Varying from season to season through the year. Compared to other commercial varieties, Sancerre has a low density of foliage.

*Internode.*—Length: about 10 cm; varies with light intensity and season.

*Size of leaf.*—Length: Long, about 11 cm. Width: Broad, about 3.5 cm.

*Shape of leaf.*—Elliptical.

*Color of leaf.*—Upper side: light green; approx. 137A-B. Under side: light green; approx. 137A-B.

*Texture.*—Smooth.

C. Rhizomes:

*Color.*—White.

*Size.*—Enlarged.

INFLORESCENCE

A. Bud:

*Form.*—Normal.

*Size.*—Diameter: About 2.5 cm just prior to opening. Length: About 4 cm.

*Receptacle.*—Broadly elliptical.

B. Flower:

*Size.*—Width: about 6 cm. Depth: about 4 cm.

*Borne.*—Umbel of about 6 branches of substantially uniform length; each bearing 3 or more buds on short peduncles.

*Blooming habit.*—When grown under controlled conditions: continuous the year around. Few blind stems are produced in fall and winter.

*Shape.*—Cupped to funnel-like.

*Outer petals.*—Shape: Heavily lobed. Size: Length: about 3 cm; Width: about 2 cm. Color: Body predominantly near to 71-D, lighter towards the attachment points of the petals, and having green tips. Reverse side: near to 71-D. Margins: Finely dentate.

*Inner petals.*—Shape: Lanceolate. Size: Upper petals: Length: about 2.5 cm; Width: about 1-1.5 cm. Bottom petal: length: about 2.5 cm; Width: about 1-1.5 cm. Color: Upper petals: predominantly creamy-white color near to 155-A in the form of a broad band occupying the central two thirds of the petal, and gradually blends into purplish-pink near to 71-D at both the apex and basal portions of each of these petals. Both upper petals have short stripes of deep purple in a uniform pattern with stripes increasing in length and width from the attachment point to the apex. Bottom petal: purple-pink near to 71-D with fewer deep purple stripes than the upper inner petals; the central portion may have lighter, washed shades of purple-pink. Reverse side: near to 71-D. Margins: Irregular undulations.

*Texture.*—Smooth.

*Peduncle.*—Color: Medium green. Length: About 12.5 cm.

*Fragrance.*—None.

*Lasting quality.*—Approximately 14 days. Petals hang on and dry.

Photoperiod control is required for continuous flower induction and production.

C. Reproductive organs:

*Stamens.*—Number: 6.

*Anthers.*—Color: Grey.

*Filaments.*—Color: Light purple.

*Pistils.*—Color: Anthocyanin. Number: 1.

*Stigma.*—Color: Light anthocyanin.

*Size.*—Typical for genus.

*Fertility.*—Not very easy.

I claim:

1. A new and distinct cultivar of Alstroemeria named Sancerre, as described and illustrated characterized by its attractive predominantly purplish-pink flowers with outer petals having green tips and substantially purplish-pink color and neither spots nor stripes; the top inner petals are purplish-pink at the base and apex and have a broad creamy-yellow band centrally; patterns of numerous purple elongated, conspicuous spots or stripes, on the top two inner petals; and, with the bottom inner petal being purplish-pink and having fewer purple stripes as compared to the top inner petal pair.

* * * * *

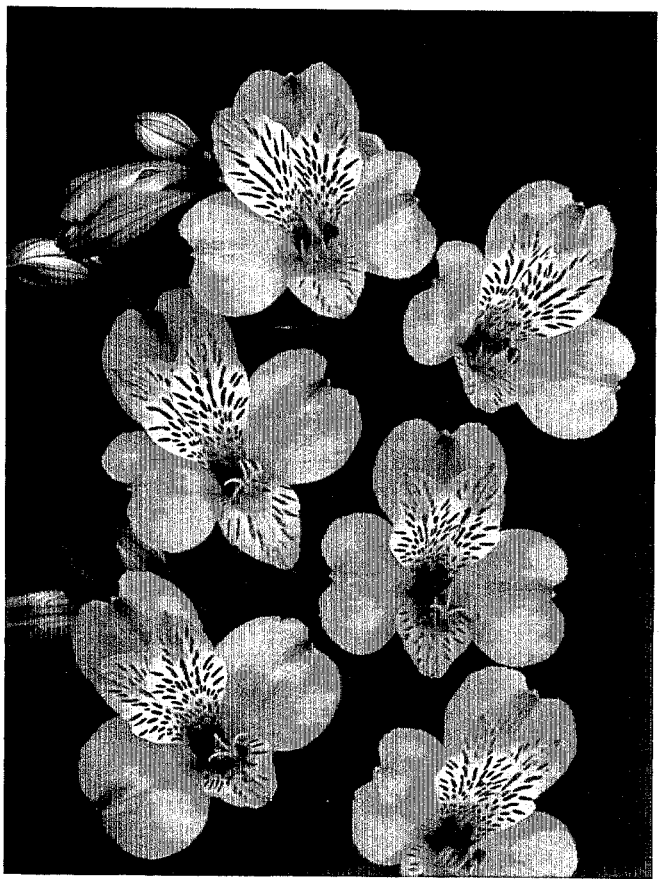

UNITED STATES PATENT AND TRADEMARK OFFICE

CERTIFICATE OF CORRECTION

PATENT NO. : PP 08,699
DATED : April 19, 1994
INVENTOR(S) : Cornelis-Theodorus-Jacobus De Jong It is certified that error appears in the above-indentified patent and that said Letters Patent is hereby corrected as shown below:

Title page, item [54], and col. 1, in the title, change "Capri" to --Sancerre'--.

Signed and Sealed this

Seventh Day of March, 1995

*Attest:*

Bruce Lehman

BRUCE LEHMAN

*Attesting Officer*

*Commissioner of Patents and Trademarks*